(12) United States Patent
Fassbind et al.

(10) Patent No.: US 6,651,305 B2
(45) Date of Patent: *Nov. 25, 2003

(54) METHOD AND APPARATUS FOR AUTOMATICALLY HANDLING A SAMPLE CUP CAP

(75) Inventors: Walter Fassbind, Baar (CH); Rolf Schnarwiler, Hochdorf (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 38 days.

This patent is subject to a terminal disclaimer.

(21) Appl. No.: 09/834,063

(22) Filed: Apr. 12, 2001

(65) Prior Publication Data

US 2001/0013169 A1 Aug. 16, 2001

Related U.S. Application Data (63) Continuation of application No. 09/162,550, filed on Sep. 29, 1998, now Pat. No. 6,216,340.

(30) Foreign Application Priority Data

Oct. 2, 1997 (EP) .............................................. 97117102

(51) Int. Cl.[7] ................................................. B23P 19/00
(52) U.S. Cl. ..................... 29/426.1; 29/426.3; 29/426.5; 29/773; 29/240; 215/356; 215/302
(58) Field of Search .............................. 29/426.1, 426.3, 29/426.5, 773, 801, 240, 267, 283; 414/411; 220/796, 801, 803, 805, 288, 293, 297, 300, 298; 901/31, 39; 215/316, 329, 356, 355, 332, 302; 81/3.07, 3.08, 3.15, 3.35, 3.29, 3.41, 3.45

(56) References Cited

U.S. PATENT DOCUMENTS

| | | | |
|---|---|---|---|
| 2,847,139 A | * | 8/1958 | Christiansson et al. ..... 215/220 |
| 3,830,390 A | * | 8/1974 | Gach .......................... 215/220 |
| 3,906,706 A | | 9/1975 | Conti |
| 4,799,599 A | * | 1/1989 | Herrmann .................... 215/307 |
| 4,984,698 A | * | 1/1991 | Stuckey ....................... 215/207 |
| 5,366,896 A | | 11/1994 | Margrey et al. |
| 5,533,407 A | | 7/1996 | Besnier |
| 5,578,494 A | | 11/1996 | Clark et al. |
| 5,586,670 A | * | 12/1996 | Greenwald ................... 215/207 |
| 5,846,489 A | * | 12/1998 | Bienhaus et al. ............ 81/3.07 |
| 6,216,340 B1 | * | 4/2001 | Fassbind et al. .............. 29/773 |

FOREIGN PATENT DOCUMENTS

| | | |
|---|---|---|
| DE | 4421220 C1 * | 11/1995 |
| EP | 0 676 643 | 10/1995 |
| GB | 2 273 493 | 6/1994 |

OTHER PUBLICATIONS

Patent Abstracts of Japan, publication No. 03226485, dated Oct. 7, 1991.

Derwent Abstract of EP 0 676 643, Accession No. 95–352514/199546.

* cited by examiner

Primary Examiner—Gregory Vidovich
Assistant Examiner—Jermie E. Cozart
(74) Attorney, Agent, or Firm—Gibbons, Del Deo, Dolan, Griffinger & Vecchione (57) ABSTRACT

An apparatus for automatically handling sample cups closed with a screwable cap is disclosed. The apparatus for automatically opening, closing and transporting sample cups comprises a transportable gripper (11) which includes a rotatable gripper tool (21) adapted to enter and engage with a recess (35, 36) of said cap (34) to form a connection which can be locked by rotating the gripper tool (21) in a first sense with respect to said sample cup (31) and which can be unlocked by rotating the gripper tool (21) with respect to said sample cup (31) in a second sense opposite to the first.

14 Claims, 7 Drawing Sheets

METHOD AND APPARATUS FOR AUTOMATICALLY HANDLING A SAMPLE CUP CAP

This application is a continuation of U.S. application Ser. No. 09/162,550, filed Sep. 29, 1998 and now U.S. Pat. No. 6,216,340B1, issued Apr. 17, 2001.

BACKGROUND OF THE INVENTION

Sample cups have to be hermetically closed preferably with a screwable cap in order to ensure that the sample contained therein cannot be contaminated by external agents and also in order to protect laboratory staff from the risk of being contaminated by a pathological sample which may be contained in the sample cup. This applies in general to sample cups used for clinical chemistry tests, and in particular to sample cups used in methods for isolating a nucleic acid sample from cell material.

According to the prior art the cap of such a sample cup has to be removed and replaced manually with great care in order to allow pipetting operations, e.g. for transferring a portion of a biological sample contained in a primary sample tube into the sample cup, before a method for isolating a nucleic acid sample from cell material is carried out on a sample contained in a sample cup; or for transferring a nucleic acid sample isolated by such a method into the sample cup.

The above mentioned manual removal and replacement of the screwable cap of sample cups is time consuming and is not compatible with the increasing need for automatic handling of sample cups in modern automatic sample cup handling apparatuses. There is therefore a need to automate the removal and replacement of the screwable caps.

There is moreover a need to transport individual sample cups closed with their respective screwable cap to different positions within the sample cup handling apparatus, e.g. in order to perform different steps of a method for isolating a nucleic acid sample from cell material.

SUMMARY OF THE INVENTION

It is therefore an object of the invention to provide an apparatus and a method and sample cups which are suitable for satisfying the above mentioned needs.

The invention concerns an apparatus for automatically handling sample cups closed with a screwable cap in a system wherein portions of biological samples contained in primary sample tubes have to be automatically pipetted into and from said sample cups.

The invention further concerns a method for automatically handling sample cups closed with a screwable cap in a system wherein portions of biological samples contained in primary sample tubes have to be automatically pipetted into and from said sample cups.

The invention further concerns a sample cup closed with a screwable cap which is adapted to be used in an apparatus and in a method according to the invention.

The invention concerns in particular an apparatus, a method and a sample cup of the above mentioned types which is suitable in particular for handling sample cups used in a method for isolating a nucleic acid sample from cell material.

According to a first aspect of the invention the aims of the invention are attained with an apparatus comprising a transportable gripper which includes a rotatable gripper tool adapted to enter and engage with a recess of said cap to form a connection which can be locked by rotating the gripper tool in a first sense with respect to said sample cup, and which can be unlocked by rotating the gripper tool with respect to said sample cup in a second sense opposite to the first.

According to a second aspect of the invention the aims of the invention are attained with an apparatus comprising a) a sample cup holder having a plurality of chambers, each of which is adapted to receive and hold the lower part of a sample cup while preventing rotation thereof, b) a plurality of sample cups, each of which is closed with a removable screwable cap and the lower part of which is inserted in one of said chambers of the sample cup holder, the outer wall of said cup having a zone the shape of which is adapted to cooperate with a corresponding zone of the inner surface of the chamber of the sample cup holder to prevent rotation of the sample cup inserted in said chamber, said screwable cap having a recess located in the top and central part of the cap, said recess comprising a slot which extends along the length axis of the sample cup and which ends in two annular channel segments which extend in opposite angular directions with respect to the length axis of the sample cup, c) a gripper movable in three orthogonal directions by a transport device, said gripper comprising a rotatable gripper tool which has an end part having a shape and dimensions which match the shape and dimensions of the recess of the cap in such a way that the end part of the gripper tool can enter through the slot of the cap's recess and by rotation enter into and engage the annular channel segments of said recess, d) a transport device for moving said gripper in said three orthogonal directions and for positioning and rotating said gripper tool to a predetermined angle within said recess of the cap of a sample cup.

According to a third aspect of the invention the aims of the invention are attained with a method for automatically handling sample cups closed with a screwable cap in a system wherein portions of biological samples contained in primary sample tubes have to be automatically pipetted into and from said sample cups, said method comprising transporting a sample cup by means of a transportable gripper which includes a rotatable gripper tool adapted to enter a recess of said cap, said transporting being effected by positioning said gripper tool in said recess, by rotating said gripper tool within said recess with respect to said sample cup until it engages and locks into said recess, and by transporting the gripper and thereby the sample cup from a first position to a second position.

According to a fourth aspect of the invention the aim of the invention is attained with a method for automatically handling sample cups closed with a screwable cap in a system wherein portions of biological samples contained in primary sample tubes have to be automatically pipetted into and from said sample cups, said method comprising removing the cap of a sample cup by means of a transportable gripper which includes a rotatable gripper tool adapted to enter a recess of said cap, said removing being effected by positioning said gripper tool in said recess, and by rotating said gripper tool within said recess in a first sense with respect to said sample cup, thereby unscrewing the cap and removing it from the sample cup.

According to a fifth aspect of the invention the aim of the invention is attained with a method for automatically handling sample cups closed with a screwable cap in a system wherein portions of biological samples contained in primary sample tubes have to be automatically pipetted into and from said sample cups, said method comprising replacing the cap of a sample cup by means of a transportable gripper which includes a rotatable gripper tool adapted to enter a recess of said cap, said replacing being effected by positioning said gripper tool in said recess, and by rotating said gripper tool within said recess in a second sense with respect to said sample cup, said second sense being opposite to said first sense, thereby screwing the cap and replacing it on the sample cup.

According to a sixth aspect of the invention a sample cup suitable to be used with an apparatus according to the invention is characterized in that it comprises a removable screwable cap which has a recess located in the top and central part of the cap, said recess comprising a slot which extends along the length axis of the sample cup and which ends in two annual channel segments which extend in opposite angular directions with respect to the length axis of the sample cup, and an outer wall having a zone adapted to cooperate with a corresponding zone of the inner surface of a chamber of a sample cup holder in order to prevent rotation of the sample cup when the lower part thereof is inserted in that chamber.

The main advantage of the apparatus, method and sample cup according to the invention is that they provide very simple and relatively inexpensive means for automatically opening, closing and transporting sample cups.

Exemplified embodiments of apparatus, method and sample cup according to the invention are described below with reference to the accompanying drawings.

DETAILED DESCRIPTION OF THE INVENTION

Figure 17:
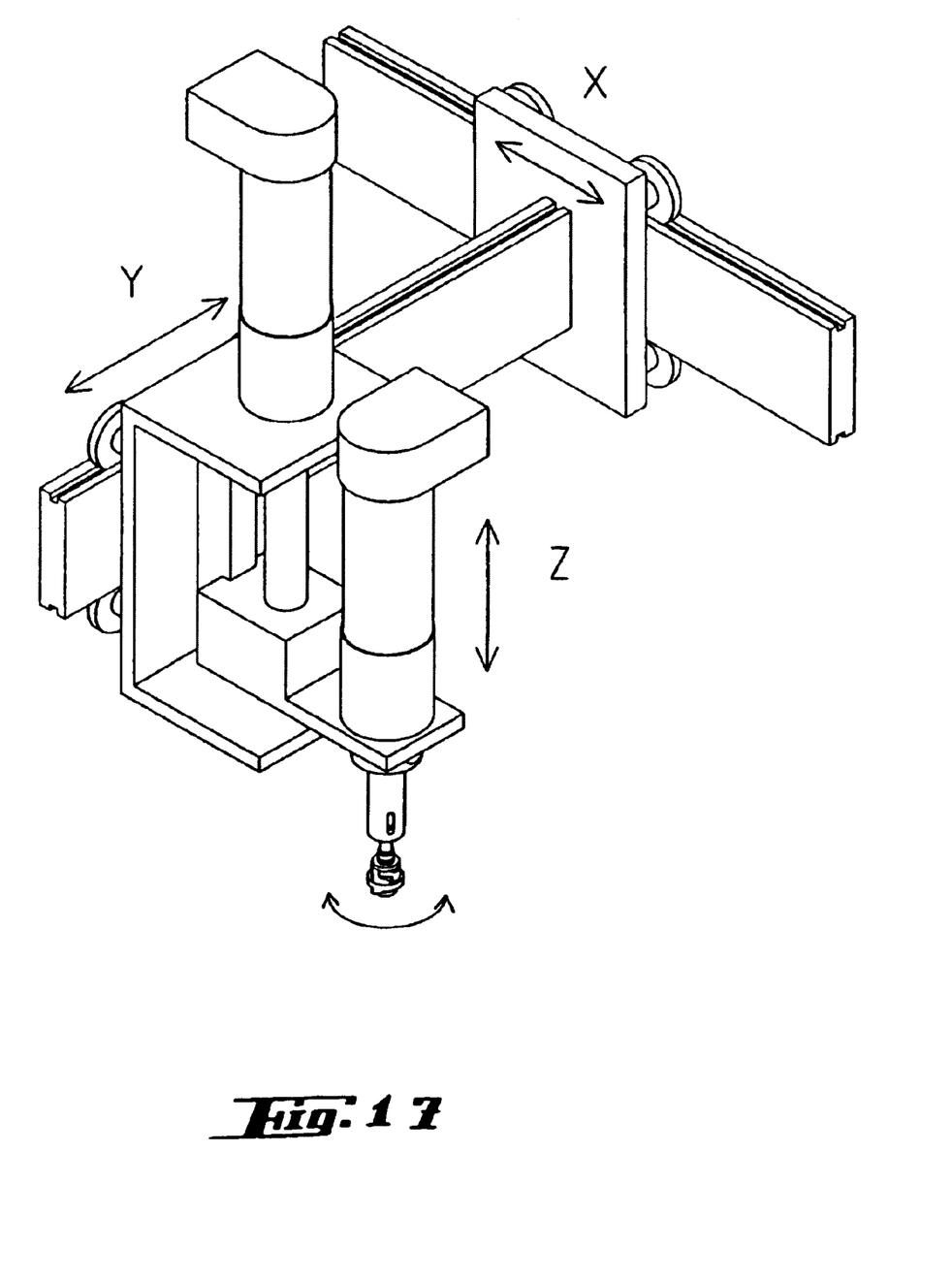
FIG. 17 schematically shows a transport device means which can move a transportable gripper in three orthogonal directions, X, Y, and Z, as well as rotate a gripper tool (21) in first and second senses.

An apparatus according to the invention comprises a transportable and rotatable gripper 11 of the type described hereinafter with reference to FIGS. 1 to 3. Transport of gripper 11 is carried out by a transport device which enables movement of gripper 11 in three directions which are normal to each other. Rotation of the gripper is carried out by a suitable controlled motor means associated with the latter transport device. The controlled motor means are such that rotation of gripper 11 and thereby of gripper tool 21 is possible in both angular senses, clockwise or counter clockwise. An example of a transport device having the means just described is schematically set forth in FIG. 17. The controlled motor means includes means for measuring variations of the amount of electrical energy associated with rotational movement of the gripper tool. In this way the apparatus is able to detect different states of its operation, e.g. when the gripper tool has engaged the recess of the cap 34 and force should be applied to unscrew cap 34 and remove it from sample cup 31.

Gripper 11 comprises a housing 12 having a top wall and a side wall which has elongated openings 13 and 13a (not shown) located on diametrically opposite sides of the side wall of housing 12, a first spring 14, and a gripper tool 21 which has a cylindrical upper part 16 which has a cavity 15 and a bottom wall connected to a shaft 25 which extends along the rotation axis of the cylindrical upper part 16 and has a lower end 24.

Pin shaped projections 17 and 17a radially extend in opposite directions from the side wall of cylindrical upper part 16. Shaft 25 has at its lower end pin shaped projections 22, 23 which radially extend in opposite directions.

An annular disk 19 is free to glide along shaft 25 between the bottom wall of cylindrical upper part 16 and pin shaped projections 22, 23. Disk 19 is however pressed against projections 22, 23 by a second spring 18 arranged with respect to shaft 25 as shown by FIG. 2.

Figure 1:
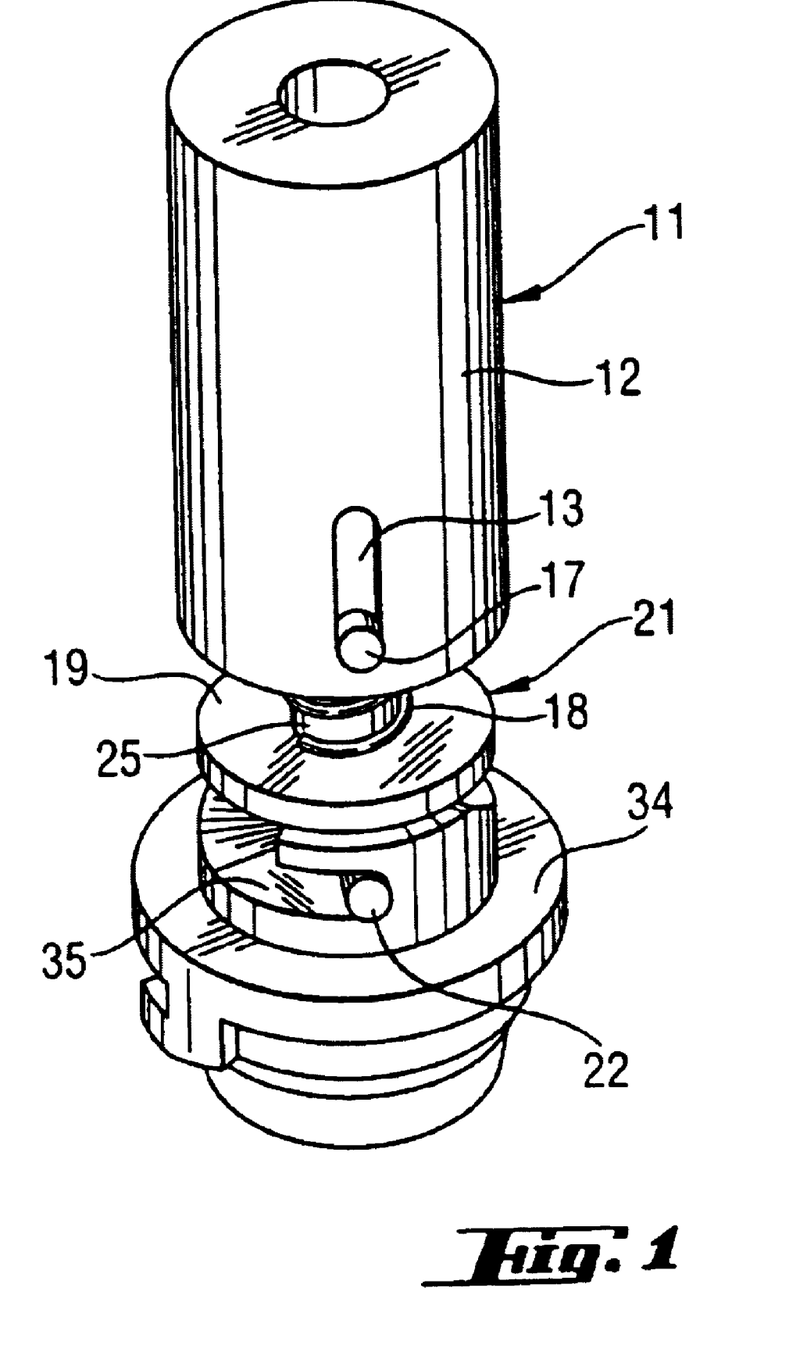
FIG. 1 shows a perspective view of a transportable gripper 11

In the assembled state of gripper 11 shown by FIG. 1, spring 14 and cylindrical part 16 are so arranged within housing 12 that pin shaped projections 17 and 17a pass through respective openings 13, 13a of housing 12, and spring 14 transmits force exerted on it by housing 12 to cylindrical upper part 16. In this way depending on the magnitude of the force applied, cylindrical upper part 16 can move within housing 12 within limits defined by the length of openings 13, 13a.

From FIGS. 1–4 and the above description it can be appreciated that when gripper 11 is rotated, gripper tool 21 rotates with it.

Figure 2:
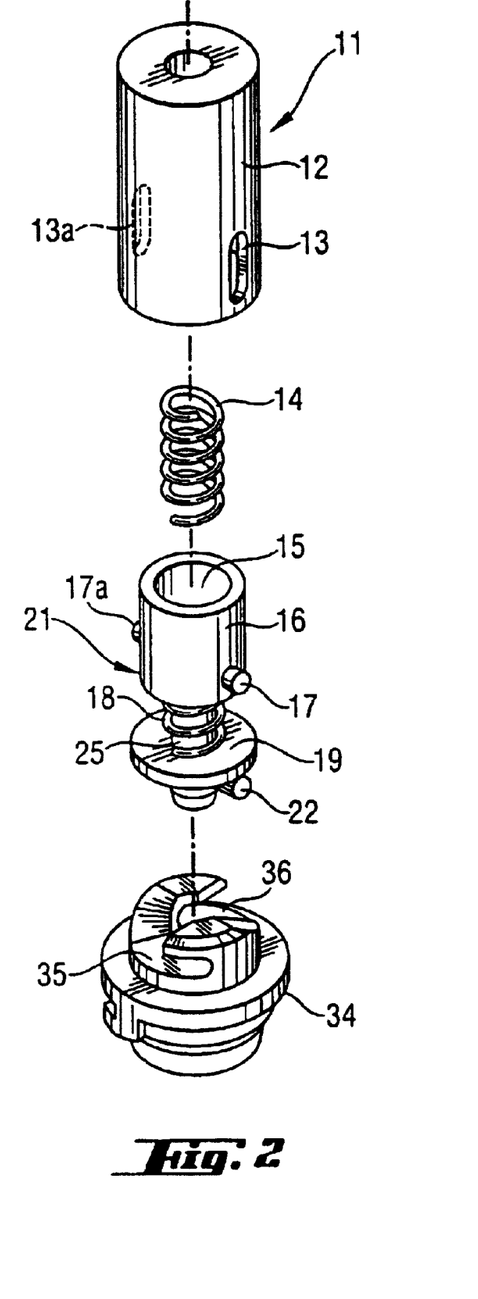
FIG. 2 shows an exploded view of the gripper 11 in FIG. 1.
Figure 3:
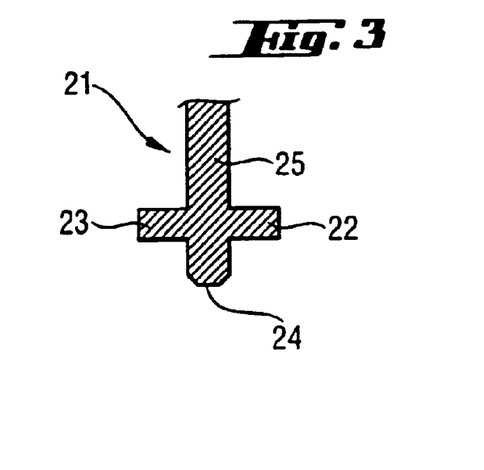
FIG. 3 is a cross-sectional view of the gripper tool 21 of gripper 11 in FIGS. 1 and 2.
Figure 4:
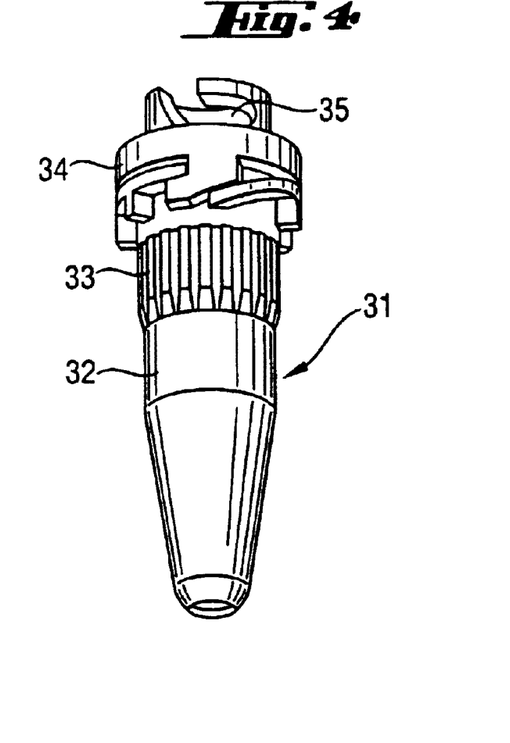
FIG. 4 is a perspective view of a sample cup 31.
Figure 5:
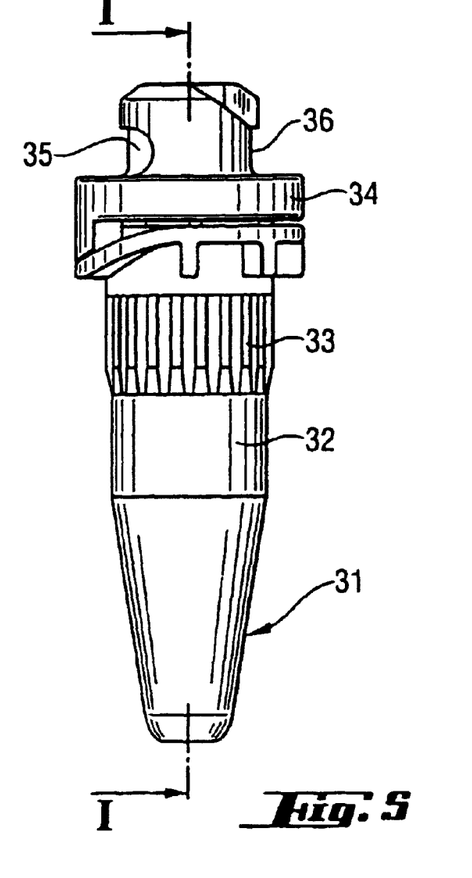
FIG. 5 is a side view of sample cup 31 in FIG. 4.
Figure 6:
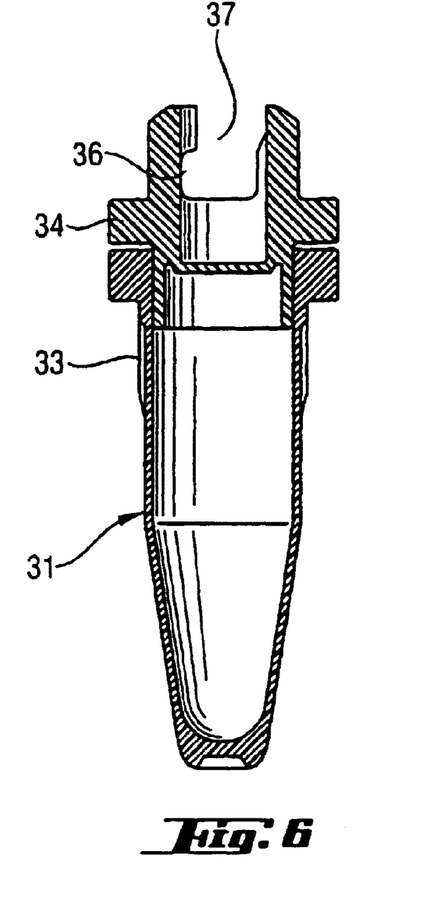
FIG. 6 is a cross-sectional view of sample cup 31 along I—I in FIG. 5.
Figure 7:
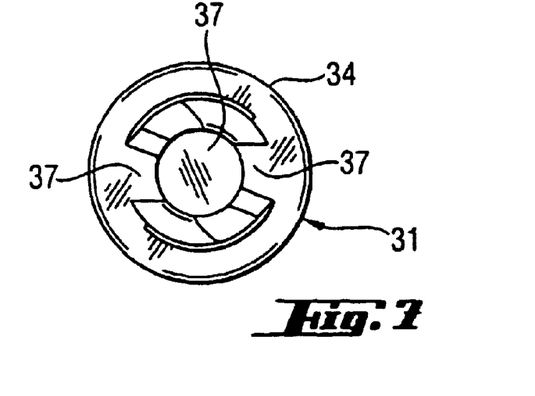
FIG. 7 is a plan view of sample cup 31 in FIG. 4.

In addition to the above described parts of gripper 11, FIGS. 1 and 2 show a cap 34 of a sample cup according to the invention.

As shown by FIG. 1, when gripper tool 21 of gripper 11 holds cap 34, spring 18 presses disk 19 against the top of cap 34, a part of which is held between disk 19 and projections 22, 23 of gripper tool 21, and the projections 22, 23 at the lower end of gripper tool 21 are engaged with recesses 35, 36 of cap 34. In FIG. 1 only recess 35 and projection 22 are shown.

FIGS. 4 to 7 show in more detail a sample cup 31 according to the invention. Such a sample cup 31 comprises a removable screwable cap 34 which has a recess located in the top and central part of the cap. This recess comprises a slot 37 which extends along the length axis of the sample cup 31 and which ends in two annular channel segments 35, 36 which extend in opposite angular directions with respect to the length axis of the sample cup 31. Sample cup 31 has an outer wall 32 which has a zone 33 the shape of which is adapted to cooperate with the shape of a corresponding zone of the inner surface of a chamber of a sample cup holder in order to prevent rotation of the sample cup 31 when the lower part thereof is inserted in that chamber.

An apparatus according to the invention comprises a rotatable gripper tool 21 which is configured and dimensioned to enter and engage with a recess 35, 36 of said cap 34 to form a connection which can be locked by rotating the gripper tool 21 in a first sense with respect to said sample cup 31 and which can be unlocked by rotating the gripper tool 21 with respect to said sample cup 31 in a second sense opposite to the first.

In a preferred embodiment now described with reference to FIG. 8 an apparatus according to the invention is used to handle a plurality of sample cups 51–69 each of which is inserted in one of a corresponding plurality of chambers of a sample cup holder 41 which has the shape shown by FIG. 8. For proper operation according to the invention the inner surface of each of said chambers has to have a zone the shape of which is adapted to cooperate with zone 33 of the outer wall of sample cup 31 in such a way that when such a sample cup is inserted in one of the chambers of sample cup holder 41, sample cup 31 is held stationary by said chamber and is not free to rotate around its length axis.

Figure 8:
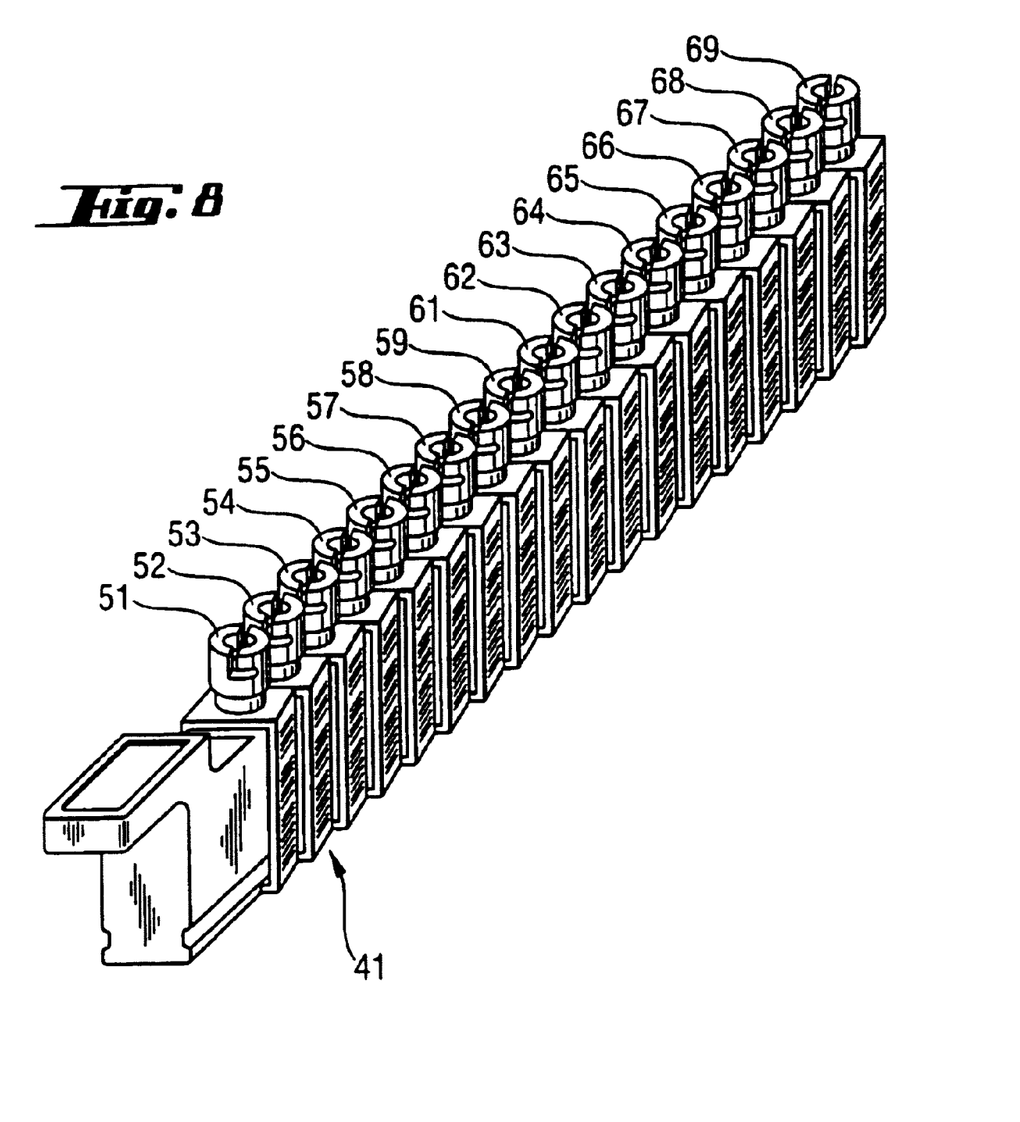
FIG. 8 is a perspective view of a sample cup holder 41 holding a plurality of sample cups.
Figure 9:
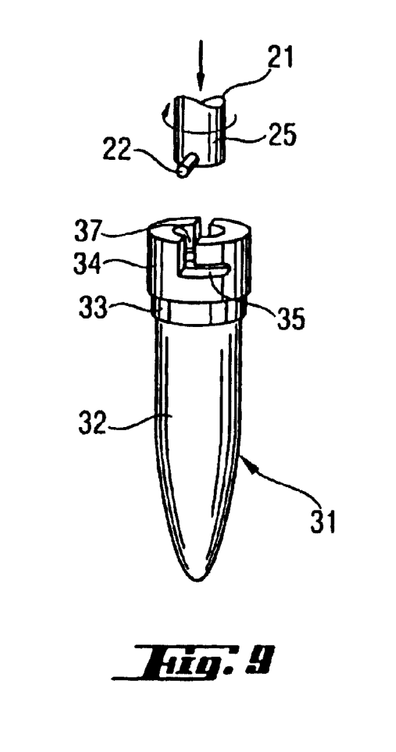
FIGS. 9 to 16 illustrate schematically various steps of methods of handling sample cups according to the invention.
Figure 10:
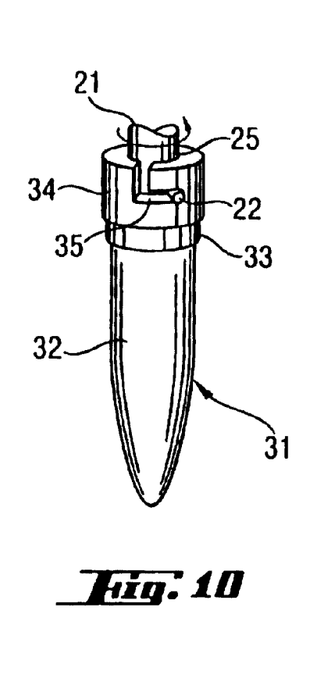

As can be appreciated from FIG. 8 the sample cups schematically shown therein are of the type described above with reference to FIGS. 4 to 7. Each of the sample cups 51–69 shown in FIG. 8 is closed with a removable screwable cap and the lower part of which is inserted in one of said chambers of the sample cup holder 41. The outer wall of each of said cups 51–69 has a zone which cooperates with a corresponding zone of the inner surface of the chamber of the sample cup holder 41 to prevent rotation of the sample cup 51–69 inserted in said chamber. The screwable cap of each of sample cups 51–69 has a recess located in the top and central part of the cap, said recess comprising a slot which extends along the length axis of the sample cup and which ends in two annular channel segments which extend in opposite angular directions with respect to the length axis of the sample cup.

An apparatus according to the invention for the above mentioned use with reference to FIG. 8 comprises a gripper of the type described above with reference to FIGS. 1–3, that is a gripper like gripper 11 movable in three orthogonal directions by a transport device. Such a gripper comprises a rotatable gripper tool which has an end part having a shape and dimensions which match the shape and dimensions of the recess of the cap of each sample cup in such a way that the end part of the gripper tool can enter through the slot of the cap's recess and by rotation enter into and engage with the angular channel segments of said recess. The transport device for moving the latter gripper is suitable for moving it in said three orthogonal directions, and for positioning and rotating the gripper tool of the gripper of a predetermined angle within the recess of the cap of each of the sample cups 51–69. An example of a transport device having the means just described is schematically set forth in FIG. 17.

A method for holding and transporting sample cups 31 closed with a screwable cap 34 with an apparatus according to the invention in a system wherein portions of biological samples contained in primary sample tubes have to be automatically pipetted into and from said sample cups is now described with reference to FIGS. 9 to 12. Such a method comprises transporting a sample cup 31 by means of a transportable and rotatable gripper which includes a gripper tool 21 adapted to enter a recess 35, 36, 37 of said cap 34, said transporting being effected by positioning said gripper tool 21 in said recess 35, 36, 37; by rotating said gripper tool 21 within said recess 35, 36, 37 with respect to said sample cup 31 until it engages and locks into said recess 35, 36, 37; and by transporting the gripper tool and thereby the sample cup 31 from a first position to a second position.

Figure 11:
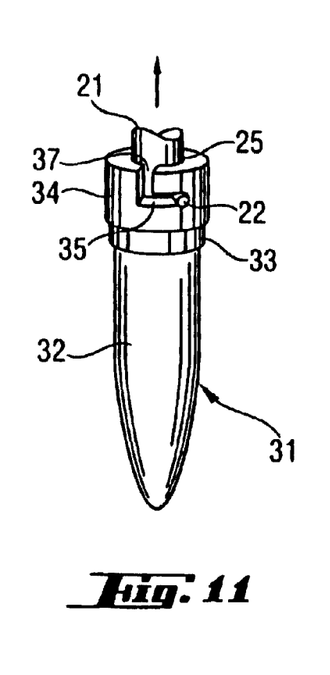
Figure 12:
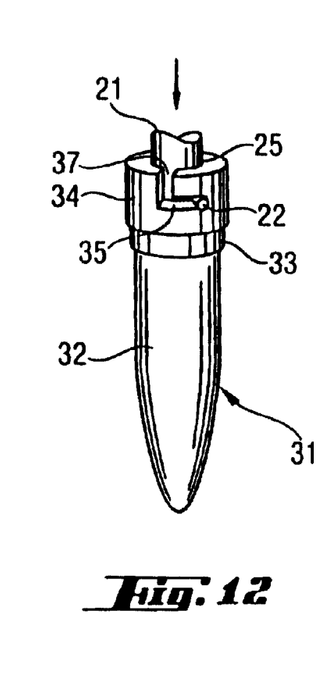

In order to position gripper tool in the recess of cap 34, gripper tool 21 is lowered by the transport means (see FIG. 17) until it contacts the upper surface of cap 34. When that contact is established, gripper tool 21 is rotated by the above mentioned controlled motor means while the transport means still exert a gentle downwards force on gripper tool 21. In this way, when the angular position of projections 22, 23 of gripper tool 21 coincides with the angular position of slot 37 of cap 34, the latter projections enter slot 37 and upon further rotation projections 22, 23 engage with annular channel segments 35, 36 of cap 34 (see FIG. 10), and in this way establish a locked connection between gripper tool 21 and cap 34, and thereby between gripper tool 21 and sample cup 31. FIGS. 11 and 12 illustrate upward and downward transport of sample cup 31 by means of gripper tool 21.

Figure 13:
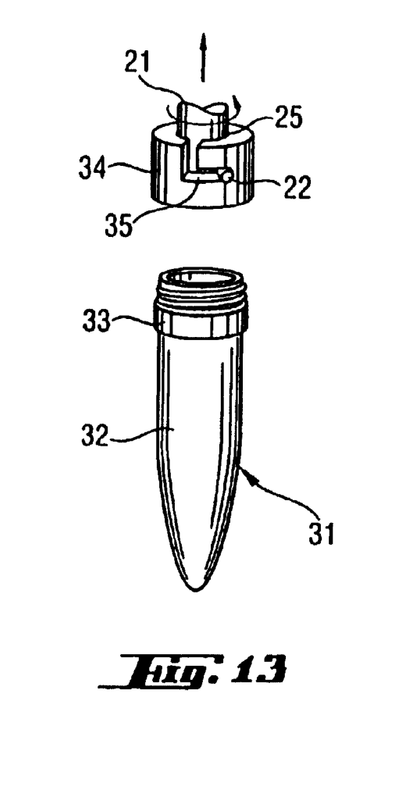

A method for removing the screwable sample cap 34 of a sample cup 31 with an apparatus according to the invention is now described with reference to FIG. 13. Such a method comprises positioning said gripper tool 21 in said recess 35, 36, 37 and rotating said gripper tool 21 within said recess 35, 36, 37 in a first sense with respect to said sample cup 31, thereby unscrewing the cap 34 and removing it from the sample cup 31.

Figure 14:
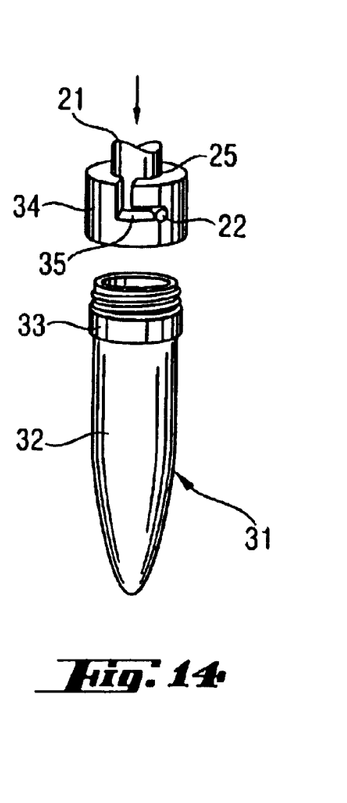
Figure 15:
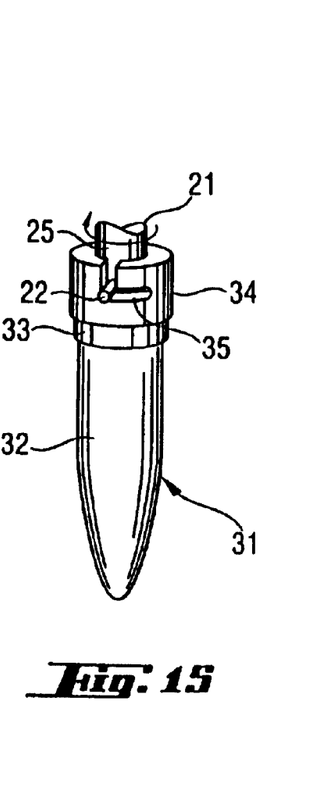

A method for replacing, i.e. for screwing a screwable sample cap 34 on a sample cup 31 with an apparatus according to the invention is now described with reference to FIGS. 14 and 15. Such a method comprises positioning said gripper tool 21 in said recess 35, 36, 37 and rotating said gripper tool 21 within said recess 35, 36, 37 in a second sense with respect to said sample cup 31, said second sense being opposite to said first sense, thereby screwing the cap 34 and replacing it on the sample cup 31.

Figure 16:
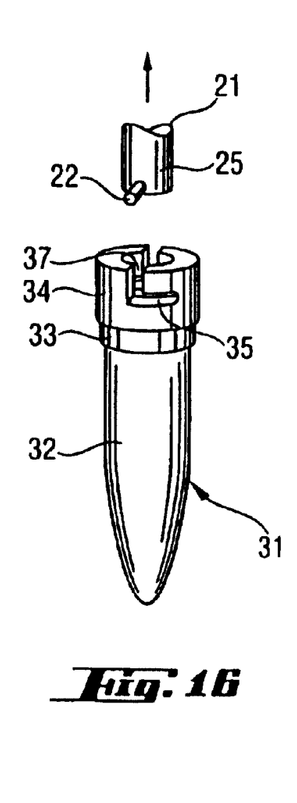

FIG. 16 illustrates how cap 34 and thereby sample cup 31 is released from gripper tool 21.

What is claimed is:

1. An apparatus for automatically handling a sample cup cap, said apparatus comprising
a gripper which includes a rotatable gripper tool having an end part that is adapted to enter and engage with a recess formed within a top part of said sample cup cap upon application of a force, said engagement of said end part and said sample cup cap forming a locked connection, by rotating the end part in a first sense with respect to said sample cup cap, in which said end part and sample cup cap are interlocked together, said engagement also forming an unlocked connection, by rotating the end part with respect to said sample cup cap in a second sense opposite to the first, in which the interlocking of said end part and said sample cup cap in the locked connection is removed, and said gripper tool has a length axis and said end part upon entering said recess is also adapted to enter two annular channel segments connected to said recess and extending therefrom in opposite angular directions with respect to the length axis.

2. The apparatus of claim 1 wherein said gripper tool further includes pin shaped projections for engaging the annular channel segments.

3. A method of handling a sample cup cap, said method comprising the steps of providing a rotatable gripper tool having an end part, applying force to cause said end part to enter into a recess formed in a top position of said cap, forming a locked connection between said end part and said sample cup cap which can be locked by rotating said end part in a first sense with respect to said cap in which said end part and said sample cup cap are interlocked to one another, and said gripper tool has a length axis and said end part upon entering said recess is also adapted to enter two annular channel segments connected to said recess and extending therefrom in opposite angular directions with respect to the length axis.

4. The method of claim 3, further comprising the step of transporting said gripper tool and locked sample cup cap from a first location to a second location.

5. The method of claim 3 wherein said sample cup cap is screwed onto a sample cup when said end part enters into said recess.

6. The method of claim 5 further comprising the step of transporting said gripper tool and locked sample cup cap screwed onto said sample cup from a first location to a second location.

7. The method of claim 5 further including step of further rotating said end part in said first sense with respect to said cap until said cap is unscrewed from said sample cup.

8. The method of claim 7 further including the step of moving said end part and locked cap away from said sample cup after said cap has been unscrewed from said sample cup.

9. The method of claim 3 further including the step of positioning said cap and end part over a sample cup with said sample cup cap in contact with and centrally disposed with respect to said sample cup.

10. The method of claim 9 further including the step of rotating said end part with respect to said sample cup cap in a second sense opposite said first sense until said sample cup cap is screwed onto said sample cup.

11. The method of claim 10 further including the step of withdrawing said end part from said sample cup cap after it has been screwed onto said sample cup.

12. A sample cup comprising a removable screwable cap which has a recess located in a top part of the cap, said cap being thereby adapted to cooperate with a rotatable gripper tool whose end part has a shape and dimensions which match the shape and dimensions of the recess of the cap in such a way that the end part of the gripper tool can enter the cap's recess upon application of a force and by rotation in a first sense with respect to said cap form a locked connection in which said end part and sample cup cap are intetlocked to one another, and said gripper tool has a length axis and said end part upon entering said recess is also adapted to enter two annular channel segments connected to said recess and extending therefrom in opposite angular directions with respect to the length axis.

13. The sample cup of claim 12 further including an outer wall having a zone which is adapted to cooperate with a corresponding zone of the inner surface of a chamber of a sample cup holder in order to prevent rotation of the sample cup when a lower part thereof is inserted in that chamber.

14. The sample cup of claim 13 wherein said zone includes a plurality of ridges.

* * * * *